`US010676744B2`

(12) United States Patent
Miranda et al.

(10) Patent No.: US 10,676,744 B2
(45) Date of Patent: Jun. 9, 2020

(54) MODULATION OF ADIPOSE TISSUE MACROPHAGE PHENOTYPE BY USE OF MICRORNA-30

(71) Applicant: University of South Carolina, Columbia, SC (US)

(72) Inventors: Kathryn Miranda, Colubmia, SC (US); Prakash Nagarkatti, Columbia, SC (US); Mitzi Nagarkatti, Columbia, SC (US)

(73) Assignee: University of South Carolina, Aiken, SC (US)

( * ) Notice: Subject to any disclaimer, the term of this patent is extended or adjusted under 35 U.S.C. 154(b) by 0 days.

(21) Appl. No.: 15/966,171

(22) Filed: Apr. 30, 2018

(65) Prior Publication Data
US 2019/0112609 A1  Apr. 18, 2019

Related U.S. Application Data

(60) Provisional application No. 62/571,847, filed on Oct. 13, 2017.

(51) Int. Cl.
  *C12N 15/113* (2010.01)
  *A61P 3/04* (2006.01)
(52) U.S. Cl.
  CPC ............ *C12N 15/1136* (2013.01); *A61P 3/04* (2018.01); *C12N 2310/113* (2013.01); *C12N 2310/141* (2013.01); *C12N 2310/3231* (2013.01)
(58) Field of Classification Search
  CPC .......... C12N 15/1136; C12N 2310/141; A01K 2207/05
  See application file for complete search history.

(56) References Cited

U.S. PATENT DOCUMENTS

| | | | | |
|---|---|---|---|---|
| 2009/0317907 A1* | 12/2009 | Esau | ............ | C12N 15/111 435/375 |
| 2012/0134929 A1* | 5/2012 | McGrath | ............ | A61K 31/10 424/9.2 |
| 2013/0072540 A1* | 3/2013 | Chen | ............ | A61K 31/713 514/44 A |
| 2014/0336240 A1* | 11/2014 | Hussain | ............ | A61K 45/06 514/44 A |
| 2016/0298113 A1* | 10/2016 | S.ae butted.trom | . | C12N 15/113 |

OTHER PUBLICATIONS

Ren et al. Adv. Nutr. 10:321-330 (Year: 2019).*
Zaragosi et al. Genome Biology 12:R63, pp. 1-13 (Year: 2011).*
Shi et al. Scientific Reports, 5:9930, pp. 1-11 (Year: 2015).*
MicroRNA in Regenerative Medicine, Chapter 21 Adipogenesis and Obesity Ramao et al. Elsevier pp. 539-565 (Year: 2015).*
Weisberg et al. J. Clin. Invest. 112: 1796-1808 (Year: 2003).*
Bam et al. "Dysreagulated immune system networks in war veterans with PTSD is an outcome of altered miRNA expression and DNA methylation." *Scientific Reports.* 6, 31209 (2016).
Bam et al. "Evidence for Epigenetic Regulation of Pro-Inflammatory Cytokines, Interleukin-12 and Interferon Gamma, in Peripheral Blood Mononuclear Cells from PTSD Patients." *Journal of Neuroimmune Pharmacology.* 11, pp. 168-181 (2015).
Bartel. "MicroRNAs: genomics, biogenesis, mechanism, and function." *Cell*, 116, pp. 281-297 (2004).
Bi et al. "Notch signaling as a novel regulator of metabolism." *Trends in Endocrinology and Metabolism.* 26, pp. 248-255 (2015).
Bi et al. "Notch signaling regulates adipose browning and energy metabolism." *Nature Medicine.* 20, pp. 911-918 (2014).
Borggrefe et al. "Fine-tuning of the intracellular canonical Notch signaling pathway." *Cell Cycle.* 11, pp. 264-276 (2012).
Boutens et al. "Adipose tissue macrophages: going off track during obesity." *Diabetologia.* 59, pp. 879-894 (2016).
Bridge et al. "The microRNA-30 family targets DLL4 to modulate endothelial cell behavior during angiogenesis." *Blood.* 120, pp. 5063-5072 (2012).
Busbee et al. "Natural Indoles, Indole-3-Carbinol (I3C) and 3,3'-Diindolylmethane (DIM), Attenuate Staphylococcal Enterotoxin B-Mediated Liver Injury by Downregulating miR-31 Expression and Promoting Caspase-2-Mediated Apoptosis." *PLOS One.* 10, e0118506 (2015).
Dong et al. "DNA methylation and atherosclerosis." *Journal of Nutrition.* 132, pp. 2406S-2409S (2002).
Freese et al. "Integrated genome browser: visual analytics platform for genomics." *Bioinformatics*, 32, pp. 2089-2095 (2016).
Fukuda et al. "Expanding role of delta-like 4 mediated notch signaling in cardiovascular and metabolic diseases." *Circulation Journal.* 77, pp. 2462-2468 (2013).
Fukuda et al. "Notch ligand delta-like 4 blockade attenuates atherosclerosis and metabolic disorders." *Proceedings of the National Academy of Sciences,* U.S.A. 109, pp. E1868-E1877 (2012).
Fung et al. "Delta-Like 4 induces Notch Signaling in Macrophages." *Circulation.* 115, pp. 2948-2956 (2007).
Ge et al. "microRNAs as a New Mechanism Regulating Adipose Tissue Inflammation in Obesity and as a Novel Therapeutic Strategy in the Metabolic Syndrome." *Journal of Immunology Research.* 2014, (2014).
Guan et al. "Inverse correlation of expression of microRNA-140-5p with progression of multiple sclerosis and differentiation of encephalitogenic T helper type 1 cells." *Immunology.* 147, pp. 488-498 (2016).

(Continued)

*Primary Examiner* — Brian Whiteman
(74) *Attorney, Agent, or Firm* — Dority & Manning, P.A.

(57) ABSTRACT

MicroRNA-30 is identified as being dysregulated in adipose tissue macrophages during obesity and can be used in treatment of disease in which adipose tissue macrophage polarization dysregulation plays a part. Increased concentration of microRNA-30, e.g., via pharmaceutical delivery, can decrease the polarization of macrophages, and in particular adipose tissue macrophages, to inflammatory M1 phenotype and can decrease expression of pro-inflammatory cytokines. One or more members of the miR-30 family can be utilized in the methods. Methods can be beneficial in treatment of a large number of inflammatory diseases including obesity, diabetes, cancer, autoimmune, etc.

19 Claims, 9 Drawing Sheets

Specification includes a Sequence Listing.

(56) References Cited

OTHER PUBLICATIONS

Hamilton et al. "Myeloid colony-stimulating factors as regulators of macrophage polarization." *Frontiers in Immunology* 5, p. 554 (2014).
Hu et al. "miR-30 Promotes Thermogenesis and the Development of Beige Fat by Targeting RIP140." *Diabetes* 64, pp. 2056-2068 (2015).
Irani et al. "MicroRNA-30c Mimic Mitigates Hypercholesterolemia and Atherosclerosis in Mice." *Journal of Biological Chemistry* 291, pp. 18397-18409 (2016).
Kent et al. "The human genome browser at UCSC." *Genome Research* 12, pp. 996-1006 (2002).
Klöting et al. "MicroRNA expression in human omental and subcutaneous adipose tissue." PLoS One 4, e4699 (2009).
Lewis et al. "Conserved seed pairing, often flanked by adenosines, indicates that thousand of human genes are microRNA targets," *Cell* 120, pp. 15-20 (2005).
Liao et al. Krüppel-like factor 4 regulates macrophage polarization. Journal of Clinical Investigation 121, 2736-2749 (2011).
Lienhard et al. "MEDIPS: genome-wide differential coverage analysis of sequencing data derived from DNA enrichment experiments." *Bioinformatics* 30, pp. 284-286 (2014).
Lumeng et al. "Obesity induces a phenotypic switch in adipose tissue macrophage polarization." *Journal of Clinical Investigation* 117, pp. 175-184 (2007).
Moore et al. "Macrophages in atherosclerosis: a dynamic balance," *Nature Reviews Immunology* 13, pp. 709-721 (2013).
Nakano et al. "Delta-Like Ligand 4-Notch Signaling in Macrophage Activation." *Arteriosclerosis, Thrombosis, and Vascular Biology* 36, pp. 2038-2047 (2016).
O'Connell et al. "MicroRNA-155 is induced during the macrophage inflammatory response." *Proceedings of the National Academy of Sciences USA* 104, pp. 1604-1609 (2007).
Pajvani et al. "Inhibition of Notch signaling ameliorates insulin resistance in a FoxO1-dependent manner." *Nature Medicine* 17, pp. 961-967 (2011).
Qiu et al. "Eosinophils and type 2 cytokine signaling in macrophages orchestrate development of functional beige fat." *Cell* 157, pp. 1292-1308 (2014).
Rao et al. "Meteorin-like is a hormone that regulates immune-adipose interactions to increase beige fat thermogenesis." *Cell* 157, pp. 1279-1291 (2014).
Shan et al. "miRNA-30e regulates abnormal differentiation of small intestinal epithelial cells in diabetic mice by downregulating Dll4 expression." *Cell Proliferation* 49, pp. 102-114 (2016).
Singh et al. "miR-155 deficiency protects mice from experimental colitis by reducing T helper type 1/type 17 responses." *Immunology* 143 pp. 478-489 (2014).
Soh et al. "MicroRNA-30c reduces hyperlipidemia and atherosclerosis in mice by decreasing lipid synthesis and lipoprotein secretion." *Nature Medicine* 19, pp. 892-900 (2013).
Sturn et al. "Genesis: cluster analysis of microarray data." *Bioinformatics* 18, pp. 207-208 (2002).
Taganov et al. "NF-κB-dependent induction of microRNA miR-146, an inhibitor targeted to signaling proteins of innate immune responses." *Proceedings of the National Academy of Sciences* 103, pp. 12481-12486 (2006).
Van Stijn et al. "Macrophage polarization phenotype regulates adiponectin receptor expression and adiponectin anti-inflammatory response," *Federation of American Societies for Experimental Biology Journal* 29, pp. 636-649 (2015).
Xiao et al. "MicroRNA Control in the Immune System: Basic Principles." *Cell* 136. pp. 26-36 (2009).
Xu et al. "Chronic inflammation in fat plays a crucial role in the development of obesity-related insulin resistance." *Journal of Clinical Investigation* 112, pp. 1821-1830 (2003).
Xu et al. "Notch-RBP-J signaling regulates the transcription factor IRF8 to promote inflammatory macrophage polarization." *Nature Immunology*. 13, pp. 642-650 (2012).
Zhang et al. "Physical activity and global genomic DNA methylation in a cancer-free population." *Epigenetics* 6, pp. 293-299 (2011).
Zhang et al. "MicroRNA-322 inhibits inflammatory cytokine expression and promotes cell proliferation in LPS-stimulated murine macrophages by targeting NF-□B1 (p50)." *Bioscience Reports* 37, BSR20160239 (2017).
Zhang et al. "Expression profiles of miRNAs in polarized macrophages." *International Journal of Molecular Medicine* 31, pp. 797-802 (2013).

* cited by examiner

MODULATION OF ADIPOSE TISSUE MACROPHAGE PHENOTYPE BY USE OF MICRORNA-30

CROSS REFERENCE TO RELATED APPLICATION

This application claims filing benefit of U.S. Provisional Patent Application Ser. No. 62/571,847 having a filing date of Oct. 13, 2017, which is incorporated herein by reference for all purposes.

FEDERAL RESEARCH STATEMENT

This invention was made with Government support under Grant Nos. R01ES019313, R01MH094755, R01AI123947, R01AI129788, P01AT003961, P20GM103641, and R01AT006888, awarded by the National Institutes of Health. The Government has certain rights in the invention.

SEQUENCE LISTING

The instant application contains a Sequence Listing which has been filed electronically in ASCII format and is hereby incorporated by reference in its entirety. Said ASCII copy, created on Jul. 15, 2019, is named USC-588_Sequence_Listing.txt and is 2,153 bytes in size.

BACKGROUND

Obesity is a pandemic disorder that is characterized by accumulation of adipose tissue and chronic-low grade inflammation driven primarily by adipose tissue macrophages (ATMs). Macrophages include a heterogeneous population of cells found in most tissues of the body. These cells are innate immune cells that are capable of performing a broad spectrum of functions. Macrophages display a remarkable plasticity between phenotypes classified along a continuum between the extremes of pro-inflammatory M1 macrophages and anti-inflammatory M2 macrophages.

It is known that ATM polarization from pro-(M1) to anti-(M2) inflammatory phenotype influences insulin sensitivity and energy expenditure, though the specific mechanisms involved are unclear. M1 macrophages are known to produce pro-inflammatory cytokines (such as IL-12, TNFα, and IL-1β), reactive oxygen species and nitric oxide, and proteases (such as MMP 2 and 9).

During obesity, M1 ATMs dominate the adipose tissue in both phenotype and abundance, promoting insulin resistance and chronic low-grade inflammation. Due to vast disparities seen in ATM functionality between lean and obese individuals, ATMs have been suggested to play a substantial role in determining development of obesity-related pathologies. Therapeutic strategies that decrease ATM-dependent inflammation have been heavily investigated due to the tight correlation of macrophage-dependent inflammation and insulin resistance.

Notch signaling is highly conserved juxtacrine signaling utilized by numerous cell types including macrophages and adipocytes and plays key roles in metabolic and inflammatory processes. Binding of Notch receptors (Notch1-4) by Delta-like and Jagged ligands (DLL1, -3, -4 and JAG1, -2) initiates proteolytic release of the Notch intracellular domain (NICD) allowing it to translocate to the nucleus and activate Jκ-Recombination Signal-Binding Protein (RBP-J)-dependent transcription.

In macrophages, Notch1 signaling promotes pro-inflammatory polarization through IRF8 and NF-κB transcriptional pathways, while in adipocytes, Notch1 signaling inhibits white adipose tissue browning and energy expenditure, and promotes insulin resistance. Additionally, blockade of the canonical Notch1 ligand DLL4 improves atherosclerosis and metabolic disease, indicating DLL4-Notch1 signaling is directly involved in the crosstalk of inflammatory and metabolic pathways.

MicroRNAs and DNA methylation have been associated with development of aging-associated pathologies including obesity, atherosclerosis, and cancer. MicroRNAs (miRNA, miR) are short (~22 nucleotide long) non-coding RNAs that post-transcriptionally inhibit protein translation by binding the 3' untranslated region (3'UTR) of target mRNAs. Because approximately 60% of protein-coding genes are known conserved targets of miRNAs, they have emerged as important regulators of biological functions such as immune system development and inflammatory responses. DNA methylation occurs when methyl groups are added to cytosines by DNA methyltransferases (DNMT). These methylated cytosines primarily reside in CpG islands near transcription start sites and repress gene transcription by blocking binding sites for transcription factors through chromatin condensation.

What are needed in the art are therapeutics for treatment of obesity related pathologies such as obesity related inflammation and insulin resistance. In particular, therapeutics including miRNAs that can be utilized in treatment of obesity-related pathologies through inhibition of polarization of ATMs to inflammatory phenotypes and/or modification of expression of inflammatory-related cytokines would be of great benefit.

SUMMARY

According to one embodiment, disclosed is a method for preferentially polarizing macrophages, and in one particular embodiment, ATMs. A method can include modifying the concentration of a microRNA-30 (miR-30) in an area that includes macrophages. An increase in the local concentration of miR-30 can lead to decreased M1 macrophage polarization, while a decrease in the local concentration of miR-30 can lead to increased M1 macrophage polarization.

According to one embodiment, methods are described for modifying expression of pro-inflammatory cytokines from a population of macrophages (e.g., ATMs). The method can include modifying the concentration of miR-30 in the population, with an increase in the concentration of miR-30 in the population leading to a decrease in the production of pro-inflammatory cytokines in the population, and a decrease in the concentration of miR-30 in the population leading to an increase in the production of pro-inflammatory cytokines in the population.

BRIEF DESCRIPTION OF THE FIGURES

A full and enabling disclosure of the present subject matter, including the best mode thereof to one of ordinary skill in the art, is set forth more particularly in the remainder of the specification, including reference to the accompanying figures in which.

DETAILED DESCRIPTION

Figure 1A:
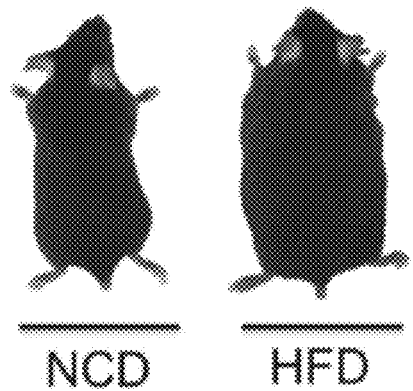
FIG. 1A illustrates mice after 16 weeks of a normal control diet (NCD) or a high fat diet (HFD).

Reference will now be made in detail to various embodiments of the disclosed subject matter, one or more examples of which are set forth below. Each embodiment is provided by way of explanation of the subject matter, not limitation thereof. In fact, it will be apparent to those skilled in the art that various modifications and variations may be made in the present disclosure without departing from the scope or spirit of the subject matter. For instance, features illustrated or described as part of one embodiment, may be used in another embodiment to yield a still further embodiment.

In general, disclosed herein are methods for utilizing microRNAs that have been identified as being dysregulated in ATMs during obesity to control the polarization of macrophages, e.g., ATMs. More specifically, disclosed methods are directed to the utilization of one or more members of the miR-30 family in control of macrophage phenotype, and specifically in control of ATM phenotype. Among other benefits, modification and control of macrophage phenotype by use of miR-30 can be utilized to modify the expression of pro-inflammatory compounds in tissue, which can be beneficial in treatment of a large number of inflammatory diseases including obesity, diabetes, cancer, autoimmune, etc.

Manipulation of the presence or concentration of one or more members of the miRNA-30 family and/or the epigenetic mechanisms that regulate the expression of members of the family can constitute therapeutic modalities for obesity-induced inflammation, insulin resistance, and related cardiometabolic disorders, among other obesity related pathologies. For instance, macrophage polarization plays key roles in regulation of both brown adipose tissue metabolism and inflammation during atherosclerosis. Thus, methods disclosed herein can include utilization of members of the miR-30 family in attenuating obesity as well as in treatment of other metabolic disorders. As utilized herein, the term "obesity" and "obese" generally refers to an individual having a body weight that is about 20% or more over an ideal body weight for that individual as determined by standard medical procedures. For instance, an obese individual can be considered an individual having a body mass index (BMI) of about 30 or greater, with BMI defined as an individual's weight in kilograms (kg) divided by their height in meters (m) squared.

Without wishing to be bound to any particular theory, it is believed that miR-30 concentration regulates pro-inflammatory polarization of ATMs via DLL4-mediated Notch1 signaling. DLL4 is a canonical Notch1 ligand that promotes M1 macrophage polarization and thus has been linked to macrophage-induced inflammation and metabolic disorders. Accordingly, regulation of the DLL4-Notch1 axis may also hold significant therapeutic potential for various inflammatory and metabolic disorders. For instance, blocking DLL4-Notch 1 signaling can lessen the effect of decreased miR-30 expression to trigger a pro-inflammatory response in macrophages According to one embodiment, macrophage M1 polarization levels can be decreased and expression of pro-inflammatory cytokines can be inhibited through increased presence of one or more members of the miR-30 family in an area including the macrophages. For instance, in one embodiment an in vivo treatment protocol is encompassed in which one or more members of the miR-30 family can be provided to a subject in need thereof, e.g., via systemic delivery, for treatment of obesity or other metabolic disorders as described. The miR-30 family contains six precursor miRNAs including mir-30a, mir-30b, mir-30c-1, mir-30c-2 mir-30d, and mir-30e that can undergo processing to generate their mature forms (e.g., miR-30a-3p, miR-30a-5p, miR-30b-3p, miR-30b-5p, miR-30c-1-3p, miR-30c-2-3p, miR-30c-5p, miR-30d-3p, miR-30d-5p, miR-30e-3p, and miR-30e-5p). Methods disclosed herein can utilize any member or combination of members of the miR-30 family.

Increased presence of one or more miR-30 family members can be obtained through delivery of the miR-30 in any form (e.g., primary microRNA, precursor microRNA, or mature microRNA). For instance, miR-30 in any useful form can be delivered to any area of interest or provided in a suitable delivery approach to a subject undergoing treatment. In one embodiment, a method can include delivery of a polynucleotide encoding a microRNA-30 in a suitable vector for transcription following delivery. An encoding polynucleotide can include genes encoding microRNA-30, primary microRNA-30 transcripts, precursor microRNA-30 transcripts, as well as mature microRNA-30. As used herein, the term "gene" generally refers to a locatable region of a genomic sequence that is involved in producing a microRNA, and includes regulatory regions, introns, transcribed regions and/or other functional sequence regions.

A miR-30 molecule or an equivalent, a mimic, or an isomiR thereof is encompassed herein and may be a synthetic or natural or recombinant or mature or part of a mature miRNA or a human miRNA or derived from a human miRNA. A human miRNA molecule is a miRNA molecule which is found in a human cell, tissue, organ or a body fluid (i.e. endogenous human miRNA molecule). A human miRNA molecule may also be a human miRNA molecule derived from an endogenous human miRNA molecule by substitution, deletion and/or addition of a nucleotide. A miRNA molecule or an equivalent or a mimic thereof may be a single stranded or double stranded RNA molecule.

A miR-30 can be delivered in unmodified form, and in one embodiment as a duplex involving complementary RNA (double-stranded RNA), chemically modified in part as 2'-O-methylpurines or 2'-fluoropyrimidines, or as asymmetrical Dicer substrates with a blunt end which includes two DNA bases and a two nucleotide overhang at the 3' end. Dicer is an endoribonuclease of the RNases III family that cleaves double-stranded RNA into short double stranded RNA fragments and catalyzes formation of the RNA-induced silencing complex. Another derivative of a miR-30 that can be utilized is double-stranded RNA chemically bound at the 3' hydroxy group to cholesterol. Further derivatives considered are known in the art, for instance those indicated in Kim D. H. and Rossi J. J., Nature Reviews Genetics, 2007, 8:173-184.

A mild-30 (or a nucleotide encoding the miR-30) can be delivered as a component of a pharmaceutical preparation comprising the miR-30 agent, and optionally a pharmaceutically acceptable carrier and optionally adjuvants. A pharmaceutically acceptable carrier may include, but is not limited to: a virus; a liposome; a nanoparticle; or a polymer, and any combination thereof. Related delivery vehicles may include, but are not limited to: liposomes, biocompatible polymers, including natural polymers and synthetic polymers; lipoproteins; polypeptides; polysaccharides; lipopolysaccharides; artificial viral envelopes; inorganic (including metal) particles; and bacteria, or viruses, such as baculovirus, adenovirus and retrovirus, bacteriophage, cosmid, or plasmid vectors.

Pharmaceutical compositions for parenteral administration, such as subcutaneous, intravenous, intrahepatic or intramuscular administration, can be utilized. A pharmaceutical composition can include from about 1 wt. % to about 95 wt. % miR-30, for instance from about 20 wt. % to about 90 wt. % of an miR-30 compound.

For parenteral administration delivery methods can include the use of solutions of miR-30, miR-30 derivatives, polynucleotides encoding miR-30, etc. and also suspensions or dispersions, such as isotonic aqueous solutions, which can be made up shortly before use. Pharmaceutical compositions may be sterilized and/or may comprise excipients, for example preservatives, stabilizers, wetting agents and/or emulsifiers, solubilizers, viscosity-increasing agents, salts for regulating osmotic pressure and/or buffers and are prepared in a manner known per se, for example, by means of conventional dissolving and lyophilizing processes. By way of example, formulations for parenteral administration may contain, for example, excipients, sterile water or saline, polyalkylene glycols such as polyethylene glycol, oils of vegetable origin, biodegradable lactide polymers, lactide/glycolide copolymers, polyoxyethlene-polyoxypropylene copolymers, ethylene-vinyl acetate copolymers, cyclodextrins, porphyrin derivatives, polyethylenimine polymers, lipofectin, atelocollagen, polylysine, nanoparticles, microspheres and liposomes, in particular liposomes formed from phospholipid bilayers, Liposomes suitable for use in delivery protocols can be formed from standard vesicle-forming lipids, which generally include neutral or negatively charged phospholipids and a sterol, such as cholesterol. The selection of lipids is generally guided by consideration of factors such as desired liposome size and half-life of liposome in the blood stream. Further considered are liposomes modified so as to avoid clearance by the mononuclear macrophages and reticuloendothelial systems, for example having opsonization-inhibition moieties bound to the surface of the liposome structures. Opsonization-inhibition moieties are large hydrophilic polymers bound to the liposome membrane, for example polyethylene glycol or polypropylene glycol and derivatives thereof, e.g., methoxy derivatives or stearates, or also synthetic polymers such as polyacrylamide or polyvinyl-pyrrolidone, linear, branched or dendrimeric polyamidoamines, polyacrylic acids, polyalcohols, e.g. polyvinyl alcohols and polyxylitol, and gangliosides.

The miR-30 related molecules can be administered alone or in combination with one or more other therapeutic agents, possible combination therapy taking the form of fixed combinations of the mild-30 related molecule and one or more other therapeutic agents known in the treatment of obesity related inflammation, insulin resistance, and/or other metabolic disorders related to the polarization of ATM. The administration of multiple therapies can be staggered or (liven independently of one another, or can be in the form of a fixed combination.

miR-30 can be used in an amount effective in one embodiment to discourage M1 ATM macrophage polarization and/or to decrease expression of pro-inflammatory cytokines in an individual. The dosage of the active ingredient will generally depend upon the age, weight, and individual condition of the subject, the individual pharmacokinetic data, and the mode of administration, as is known. In the example of an individual human having a bodyweight of about 70 kg, a daily dose of and administered microRNA-30 can be from about 0.01 mg/kg bodyweight to about 100 mg/kg bodyweight, for instance from about 0.1 mg/kg bodyweight to about 50 mg/kg bodyweight, or from about 1 mg/kg to about 20 mg/kg bodyweight administered as a single dose or as several doses.

The present disclosure may be better understood with reference to the Examples set forth below.

EXAMPLE

Materials and Methods
Mice 6- to 8-week-old male and female C57Bl/6J mice and 22-week-old male C57Bl/6J mice fed either 60% kcal HFD (D12492, Research Diets), normal control diets (NCD) (8904, Envigo Teklad), or purified 10% low-fat diet (LFD, D12450J, Research Diets for 16 weeks were obtained from The Jackson Laboratory and housed in a specific-pathogen-free facility. Studies were not blinded and mice were not randomized into experimental groups. At the conclusion of each study, mice were euthanized by overdose isoflurane inhalation.

Analytical Procedures

Body composition of lean mass, fat mass, and percent fat were measured by dual-energy x-ray absorptiometry (DEXA) (LUNAR PIXImus). Mice were placed under isoflurane anesthesia and scanned in the prone position with the head region being excluded. Body weight was monitored using an electronic gram scale with precision ±0.1 g. For glucose tolerance tests, mice underwent a 5 hr morning fast before fasting glucose measurement then gavaged with 2 g/kg lean mass glucose (Sigma G7528). Blood glucose was measured 15, 30, 60 and 120 m post-glucose bolus by applying approximately 5 µL tail-tip blood to a glucose test strip in a glucose meter (Contour Next, Bayer).

Adipose Tissue Dissociation and ATM Isolation

To dissociate cells of the stromal vascular fraction (SVF), epididymal fat pads from 22 week-old mice were dissected, rinsed in phosphate buffered saline (PBS) and homogenized in 5 mL digestion media consisting of Hank's Balanced Salt Solution (HBSS) containing 2% bovine serum albumin (BSA) and 1 mg/mL collagenase (Sigma C6885) using a gentle MACs dissociator (Miltenyi Biotec). An additional 5 mL digestion media was added to the homogenates and incubated 37° C., 75 RPM, 30-40 m until fully dissociated. Next, 5 mL complete Dulbecco's Modified Eagle's Medium and Ham's F-12 Nutrient Mixture (DMEM/F12) containing 10% FBS and 1% penicillin/streptomycin was added to the samples before filtering through a 100 um nylon mesh. SVF cells were pelleted (1200 RPM, 4° C., 10 m), RBC-lysed, filtered through a 70 µm nylon mesh and washed in complete DMEM/F12 then used immediately for desired application. To purify ATMs, SFV cells were washed twice in FACS buffer consisting of PBS, 2% heat-inactivated fetal bovine serum (FBS), and 1 mM EDTA then incubated in FcR-Blocker (StemCell Tech, 18720) followed by PE-conjugated anti-F4/80 (BioLegend, Clone BM8). F4/80+ cells were immune-magnetically selected by EasySep PE positive selection kit according to manufacturer protocol including 4 total wash steps (StemCell Tech, 18557). Flow cytometry was used to verify selection purity, which was greater than 85%.

RNA Purification, cDNA Synthesis, and Quantitative RT-PCR

ATMs were lysed in Qiazol and total RNA was purified using Qiagen miRNeasy Microkit. RNA concentration and purity were measured using a NanoDrop 2000 spectrophotometer. 400 ng total RNA was reverse transcribed to cDNA using Qiagen miScript II RT kit with HiFlex buffer. To validate miRNA expression by qRT-PCR, miScript SYBR Green PCR kit and miScript miRNA Primer Assays were used (Qiagen).

ATM MicroRNA and Transcriptome Microarrays

MicroRNA and transcriptome microarrays were performed using 3 biological replicates of total RNA isolated from pools of ATMs (NCD: pools of 20 mice, HFD: pools of 10 mice). For each miRNA microarray, 500 ng total RNA was polyadenylated then labeled using the Affymetrix FlashTag Biotin HSR RNA Labeling Kit. Labeled samples were hybridized to Affymetrix miRNA 4.0 chips overnight (16 h, 48° C., 60 RPM) then washed, stained, and scanned on an Affymetrix GCS 3000 system following manufacturer protocols. For transcriptome microarrays, 100 ng total RNA was used as starting material. RNA was prepared for hybridization by using the Affymetrix GeneChip WT PLUS Reagent Kit according to manufacturer protocol. Labeled samples were hybridized to MTA 1.0 chips overnight (16 h, 45° C., 60 RPM) then washed, stained, and scanned on an Affymetrix GCS 3000 system. Affymetrix Expression Console Version 1.4.1.46 was used for quality control, data summarization, and normalization. Affymetrix Transcriptome Analysis Console Version 3.1.0.5 was used to perform differential expression analyses. Transcripts or miRNAs were considered differentially expressed between the two groups if linear fold change was greater than ±2 and the ANOVA p-value was less than 0.05. Heatmap figures of differentially expressed microRNAs and RNAs were made using Genesis Version 1.7.7.21

Immunofluorescence

Epididymal fat was dissected, minced (~3 mm×3 mm), washed in PBS, and then fixed in 4% paraformaldehyde for 3 h. Fixed tissues were permeabilized with 1% Triton X-100 for 10 min then blocked with 1% BSA and FcR-Blocker for 1 h at RT. Samples were incubated with primary antibody (BioLegend: anti-F4/80-AlexaFluor488 clone: BM8, and anti-Notch1 clone: HMN1-12, or anti-DLL4 clone: HMD4-1) overnight at 4° C., then incubated with anti-Hamster IgG-AlexaFluor633 secondary antibody for 1 h at RT (Invitrogen SA1-26817, Molecular Probes labeling kit A20170). Tissues were counterstained with 40 µM Hoechst 33342 and 5 uM BODIPY 558/568 C12 (Molecular Probes H21492 & D3835) for 1 h at RT then washed and mounted on slides using a Vaseline boundary and Fluoromount-G (eBioscience, 00-4958-02).

Confocal Microscopy and Image Analysis

Confocal images of whole-mount adipose tissue were acquired on a Zeiss LSM 510 Meta Confocal Scanning Laser Microscope equipped with UV, Argon, green HeNe and red HeNe lasers. 5 random images per sample were taken using a 40× water immersion objective. Original .lsm files were imported into Fiji (Fiji Is Just ImageJ, NIH) then split into channels. Thresholds were applied to the Cy5 channel using Fiji's max Entropy algorithm to identify regions of interest (ROIs) that express either Notch1 or DLL4. Area and intensity (mean gray value) were measured for each ROI. The product of positive signal area and intensity were used to determine total expression per image. Each biological replicate is the mean expression of 5 images. The expression values were then divided for each biological replicate by the mean of the NCD biological replicates. Therefore, data were presented as fold expression in arbitrary units (AU) with mean NCD set as control.

Flow Cytometry

Freshly isolated SVF cells or cultured BMDM were washed in FACS buffer then incubated on ice with FcR-Blocker for 10 m followed by appropriate fluorochrome-conjugated antibodies or isotype controls (BioLegend, anti-CD11b-AlexaFluor488 clone: M1/70, anti-F4/80-PE clone: BM8, anti-DLL4-APC clone: HMD4-1, anti-CD45-PECy7 clone: 30-F11, anti-CD11c-APC clone: N418) for 50 m. Stained cells were washed 3× in FACS buffer then analyzed on a Beckman Coulter FC500 or BD FACSCelesta flow cytometer. Plots were analyzed with Beckman Coulter CXP Software or FlowJo v10.

In Vitro Locked Nucleic Acid (LNA) Transfection Assays

Bone marrow derived macrophages (BMDM) were differentiated from bone marrow cells (BMC) by flushing the tibia and femur of 6-8 week old female C57Bl/6J mice with PBS. BMCs were filtered through a 70 µm nylon mesh, RBC-lysed, and washed, then cultured in complete DMEM/F12 supplemented with 10% FBS, 1% penicillin/streptomycin, 2 mM L-glutamine, and 1 U/mL M-CSF (BioLegend, 576406) for 7-10 days. 3T3-L1 adipocyte-conditioned media (CM-3T3-L1A) was generated by differentiating 3T3-L1 preadipocytes into adipocytes according to the Zen-Bio 3T3-L1 Adipocyte Care Manual (ZBM0009.03). Preadipocyte medium, differentiation medium, and adipocyte maintenance medium were also used (Zen-Bio, PM-1-L1, DM-2-L1, AM-1-L1). Conditioned medium was collected between days 7 and 14 post-differentiation, 0.22 µm filtered, aliquoted, and stored at −80° C. until use. For transfection assays, mature BMDM were plated in poly-D-lysine-coated 6-well plates at a density of $5 \times 10^5$ cells in 2 ml CM-3T3-L1A containing 10% FBS without antibiotics. BMDM were incubated 24 h (37° C., 5% $CO_2$, 95% humidity) before transfection. Transfection complexes were prepared by diluting Lipofectamine3000 and LNA in Opti-MEM to final concentrations of 2% (v/v) and 0.32 µM respectively. Mixtures were incubated 15-20 m at RT to allow complexes to form. Meanwhile, conditioned BMDM were washed 3× in pre-warmed Dulbecco's PBS (DPBS), then media replaced with 2 mL Opti-MEM. 5004 transfection complexes were added drop-wise to each well. Cells were incubated (37° C., 5% $CO_2$, 95% humidity) 5-6 hr to allow LNA uptake, washed 3× in pre-warmed DPBS, then media replaced with DMEM/F12 containing 10% FBS, 1% penicillin/streptomycin, and 2 mM L-glutamine, and cultured for an additional 18 h. For inhibition studies, DAPT (5 uM), anti-DLL4 antibody (1 ug/mL), or appropriate vehicle/isotype antibody controls were added to the culture media. MirCURY LNA oligonucleotides were obtained from Exiqon. LNA Sequences:

```
Ctr LNA:
                              (SEQ ID NO: 1)
TAACACGTCTATACGCCCA

Anti-30a:
                              (SEQ ID NO: 2)
TTCCAGTCGAGGATGTTTAC

Anti-30c:
                              (SEQ ID NO: 3)
CTGAGAGTGTAGGATGTT

Anti-30e:
                              (SEQ ID NO: 4)
TCCAGTCAAGGATGTTTAC
```

Protein Extraction and Western Blotting

Cultured BMDM were washed twice in ice-cold PBS, and then directly scrapped into 100 µL blue loading buffer (Cell Signaling Tech 7722) and kept on ice. Protein lysates were sonicated 10 s then heated at 95° C. for 5 m before loading 20 µL on Mini-Protean TGX Protein Gels (BioRad 4569034). Precision Plus Protein Dual Color Standards (BioRad 1610374) were loaded for a molecular weight ladder. Samples were run 40V for 30 min followed by 80V for 1.5 h. Proteins were transferred to nitrocellulose membranes by using iBlot 2 NC stacks and the ThermoFisher iBlot 2 western transfer system running the P0 protocol (20V 1 m, 23V 4 m, then 25V 2 m). Membranes were blocked in 5% dry milk or 5% BSA for 1 h then washed 3× in Tris-buffered saline containing 0.1% Tween-20 (TBS-T). Membranes were incubated in primary antibody overnight at 4° C. with gentle shaking then washed 3×5 m in TBS-T. Membranes were incubated in secondary antibody for 1 h at RT, then washed 3×5 m in TBS-T before addition of ECL substrate and exposure to x-ray film. Films were scanned and densitometry measurements were made using ImageJ gel analysis features (NIH).

Enzyme-Linked Immunosorbent Assays (ELISA)

Culture supernatants were aspirated and centrifuged 5000 RPM, 5 m, 4° C. to rid of debris then aliquoted and stored −80° C. before assaying. DLL4 ELISA kits were purchased from Abcam (ab213860). Mouse TNFα and CCL2 ELISA kits were purchased from BioLegend (TNFα 530901 & CCL2 432701). Assays were performed according to manufacturer protocols and plates were read at 450 nm. Concentrations were calculated using standard curves.

Methylated DNA Immunoprecipitation Sequencing (Me-DIP-Seq)

MeDIP-seq libraries were generated from ATM DNA and sequenced with single-end reads of 75 bp on an Illumina NextSeq500. Mapped reads were analyzed using MEDIPS software. Peaks were visualized in the Integrated Genome Browser. The UCSC genome browser was used to locate CpG islands within 10 kb of miR-30 gene coding regions.

Methylation-Specific PCR

Genomic DNA from NCD and HFD ATMs were isolated using Qiagen AllPrep DNA/RNA/miRNA Universal Kit (80224). Bisulfite conversion of DNA was performed using Qiagen EpiTect Fast DNA Bisulfite Kit (59824). PCR was performed using the following methylated and unmethylated primers specific for the Nfyc CpG island:

```
Methylated:
                                    (SEQ ID NO: 5)
Fwd-TTCGTTAATGGGAGAAAGTTC (SEQ ID NO: 6)
Rev-CTACCGCCGCCATATTATA Unmethylated:
                                    (SEQ ID NO: 7)
Fwd-TTTTTTGTTAATGGGAGAAAGTTT (SEQ ID NO: 8)
Rev-ACTCTACCACCACCATATTATA
```

Primers were designed using ThermoFisher Methyl Primer Express Software v1.0. BioRad iQ SYBR Green Supermix was used and qRT-PCR was run using the following reaction conditions: initial denaturation—95° C. 5 m followed by 31 cycles of −95° C. 15 s, 49.8° C. 30 s, and 70° C. 35 s. PCR products were run on a 1.5% agarose gel and bands were quantified using FIJI gel analysis features. Methylation ratio was determined by dividing methylated by unmethylated quantities (M/U).

Statistical Analysis

Statistical analyses were performed using GraphPad Prism Version 7.000 for Mac, GraphPad Software, La Jolla, Calif. USA. Values are expressed as mean±standard error. Two-tailed Student's t tests were performed for paired analyses. One-way ANOVA with a Bonferroni post hoc correction were used for multiple group analyses. The null hypothesis was rejected if p<0.05. All experiments were repeated at least twice, unless otherwise indicated in each figure legend. Detailed sample sizes are provided in each figure legend. Sample sizes were chosen by power analysis based on pilot studies.

Results

Figure 1B:
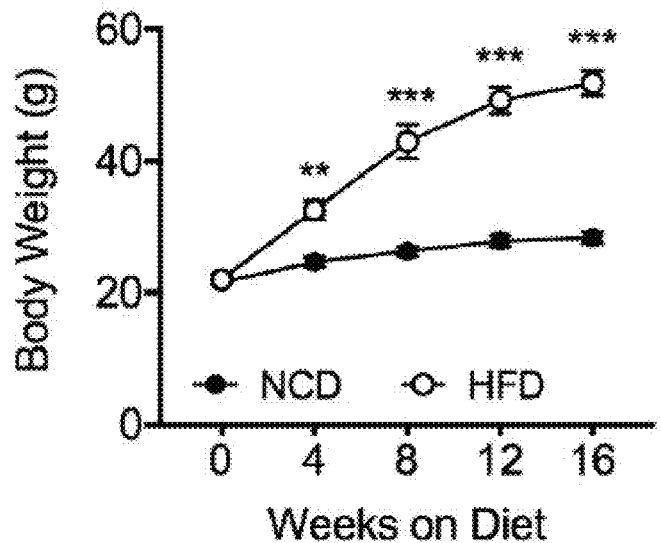
FIG. 1B presents weekly measurements of body weight growth of the mice over the course of the diet.
Figure 1C:
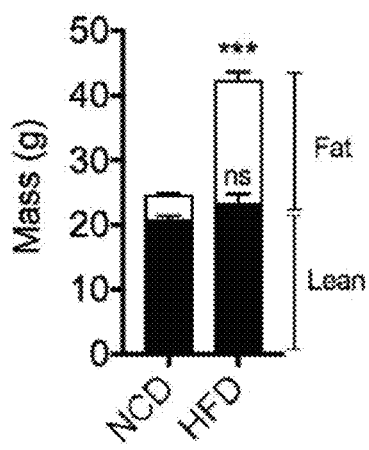
FIG. 1C presents the dual-energy x-ray absorptiometry (DEXA) body composition of the mice after 16 weeks of diet.
Figure 1D:
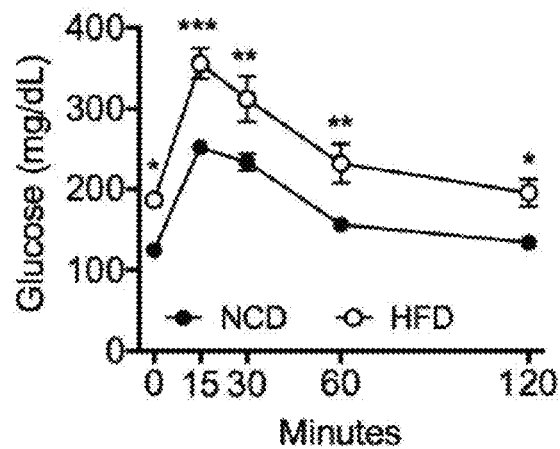
FIG. 1D presents the results of the oral glucose tolerance test (GTT) after 16 weeks of diet.
Figure 1E:
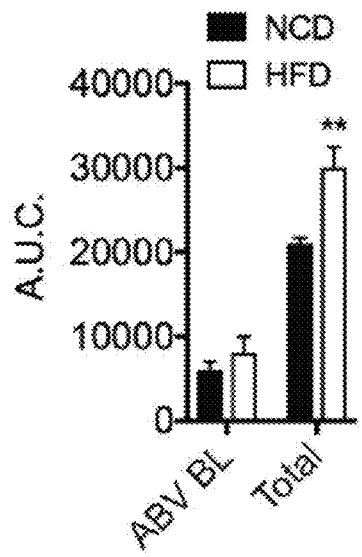
FIG. 1E illustrates the area under the curve (A.U.C.) for GTT of FIG. 1D. Represented are A.U.C. above baseline (ABV BL) or total A.U.C.

HFD-fed mice more than doubled their body weight during 16 weeks of feeding whereas NCD-fed mice increased their weight by ~3% (FIG. 1A, FIG. 1B, FIG. 1C), and HFD-induced weight gain occurred due to selective increases in fat mass (FIG. 1C). As expected, HFD also caused glucose intolerance measured by glucose tolerance test (GTT) (FIG. 1D, FIG. 1E).

Figure 1F:
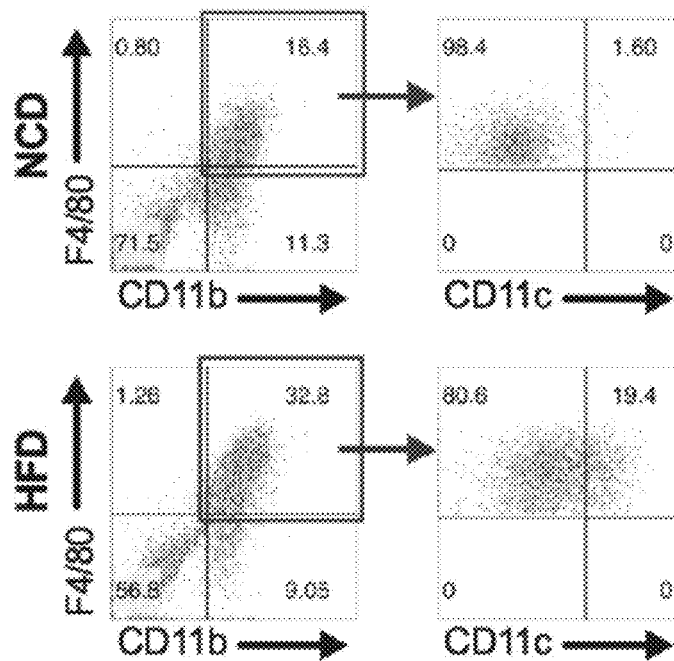
FIG. 1F includes flow cytometry dot plots of F4/80+/CD11b+/CD11c+ ATMs in the epididymal fat stromal vascular fraction (SVF) of NCD- or HFD-fed mice. For FIG. 1A-FIG. 1F, the values are shown as mean±SEM and are from a single experiment representative of at least 3 independent experiments with 5 mice per experimental group.
Figure 1G:
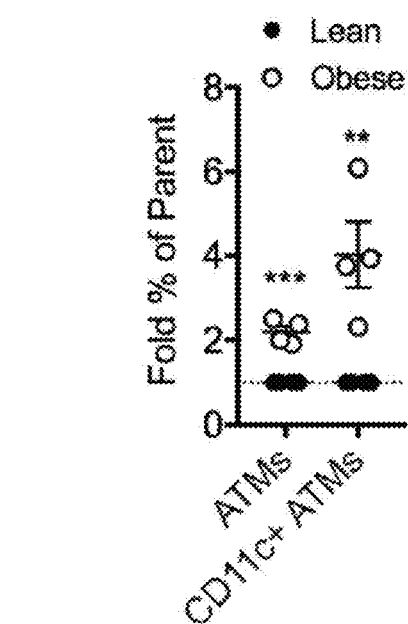
FIG. 1G illustrates the fold percentage increase quantification of F4/80+/CD11b+cells in the SVF (denoted as "ATMs") and CD11c+ ATMs. Lean mice were fed either NCD or 10% low-fat diet (LFD). Obese mice were fed 60% HFD. Data is shown as mean±SEM of 4 independent experiments with 5 mice per experimental group.
Figure 1H:
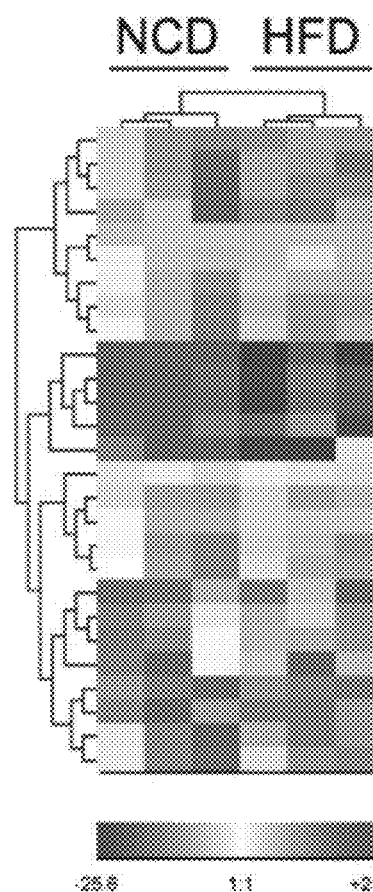
FIG. 1H presents a transcriptome microarray heatmap of differentially expressed mRNAs related to macrophage polarization obtained from pooled F4/80+ ATMs from epididymal fat.

While phenotyping ATMs, it was observed that percentages of ATMs (F4/80+/CD11b+) and CD11c+ ATMs in epididymal fat of obese mice were more than 2 and 4 fold that of lean mice respectively (FIG. 1F, FIG. 1G). To identify gene expression alterations in HFD and NCD ATMs transcriptome microarrays were performed using F4/80+ cells from epididymal fat of HFD and NCD mice. Principal component analysis (PCA) displayed HFD and NCD ATMs have distinct transcript expression profiles. HFD ATMs exhibited increased M1- and decreased M2-associated gene expression (FIG. 1H). Notably, Irf8, which encodes a transcription factor activated by Notch-RBPJ signaling, as well as Itgax, which encodes the M1 surface marker CD11c, were upregulated in obese ATMs. Alternatively, Klf4, which encodes Krüppel-like factor 4 that cooperates with STAT6 to promote M2 polarization, and Adipor2, which encodes a receptor for the anti-inflammatory adipokine adiponectin, were downregulated in obese ATMs. Together these observations suggested that HFD ATM phenotype was skewed toward M1.

Figure 1I:
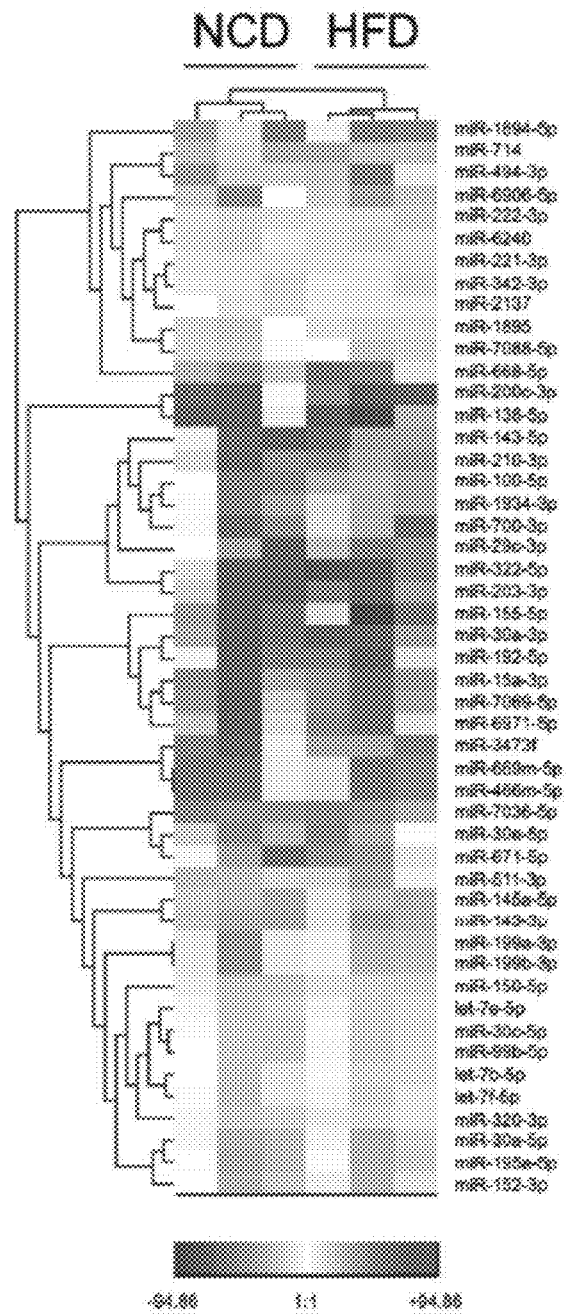
FIG. 1I presents a microRNA heatmap of differentially expressed miRNAs in ATMs obtained from pooled F4/80+ ATMs from epididymal fat.
Figure 1J:
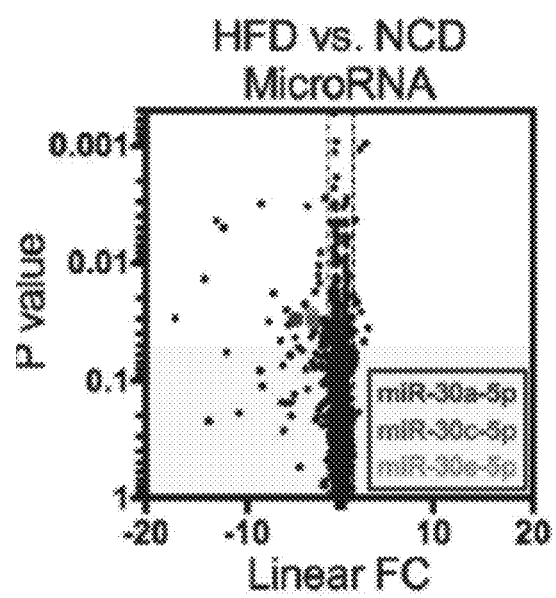
FIG. 1J presents a microRNA array volcano plot depicting linear fold change (FC) vs. ANOVA p-value significance obtained from pooled F4/80+ ATMs from epididymal fat.
Figure 1K:
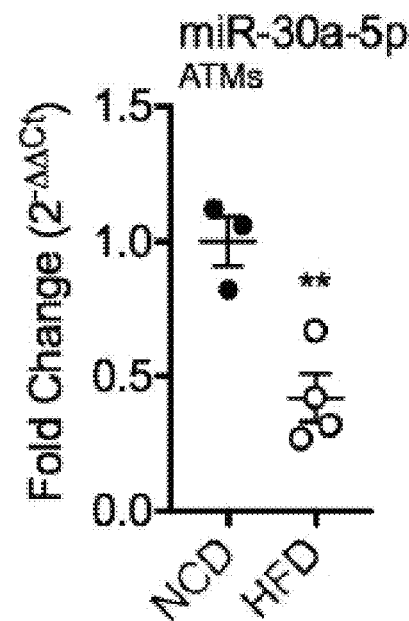
FIG. 1K, presents qRT-PCR expression validation of miR-30a-5p.

To identify differentially expressed miRNAs in ATMs during obesity, miRNA microarrays were performed using F4/80+ cells isolated from epididymal fat of HFD and NCD mice. PCA showed HFD and NCD ATMs have distinct miRNA expression profiles. In total, there were 37 down- and 12 up-regulated miRNAs in HFD versus NCD ATMs (FIG. 1I, FIG. 1J). Additionally, transcriptome microarrays showed there were 946 down- and 920 up-regulated transcripts in HFD versus NCD ATMs. Of these, 216 and 273 coding genes were up- and down-regulated respectively. Core analyses were performed on these dysregulated miRNAs and transcripts using Ingenuity Pathway Analysis and significant overlap was observed with canonical pathways including hepatic fibrosis and atherosclerosis signaling, disorders such as cancer and hepatic disease, cellular functions including movement and survival, and toxic effects including cardiotoxicity, hepatotoxicity, and nephrotoxicity.

Figure 1L:
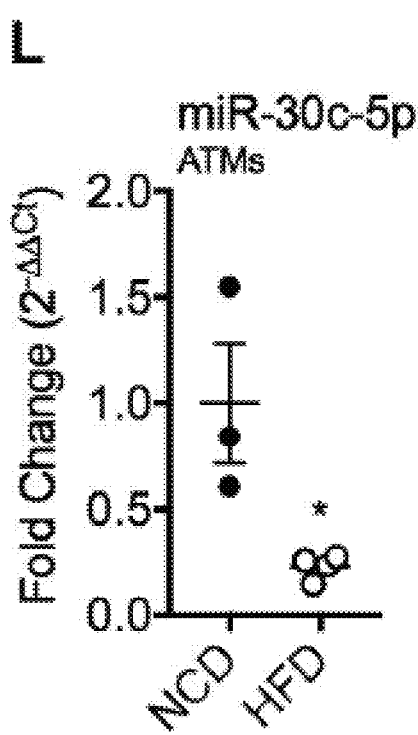
FIG. 1L presents a qRT-PCR expression validation for miR-30c-5p.
Figure 1M:
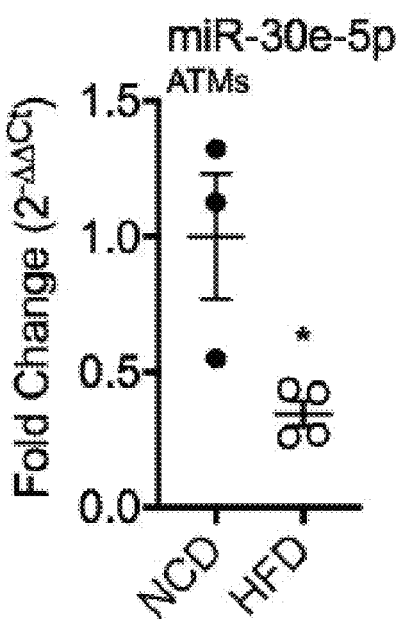
FIG. 1M presents a qRT-PCR expression validation for miR-30e-5p. For FIG. 1H through FIG. 1M, the data shown are mean±SEM and are from 3-4 independent experiments with 20 pooled NCD mice and 10 pooled HFD mice per experiment. Statistical differences were determined by using Student's t-test. $*p<0.05$, $p<0.01$, $*p<0.001$.

Upon closer examination of dysregulated miRNAs during obesity, downregulation of miR-322-5p (−17.1 linear FC) and miR-155-5p (−14.19 linear FC) was observed, which have been previously characterized for their involvement in macrophage functions. Downregulation of miRs-30a-5p, -30c-5p, and -30e-5p in HFD ATMs was also noted (−12.27 combined linear FC) when compared to NCD ATMs, thereby indicating that the miR-30 family may play a role in macrophage polarization (FIG. 1L, FIG. 1M).

Figure 2A:
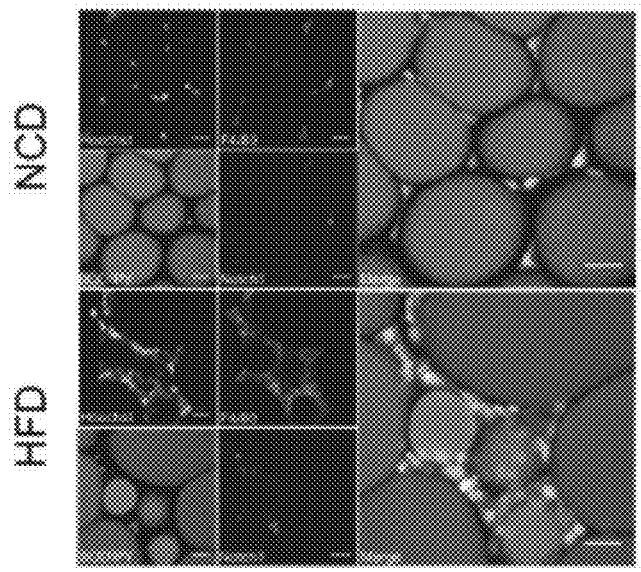
FIG. 2A presents confocal micrographs of Notch 1 staining of whole mount epididymal fat (scale bar=20 μm).
Figure 2B:
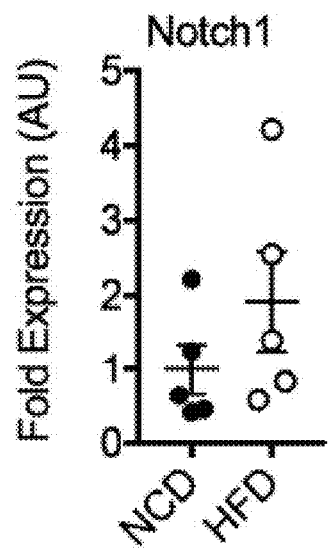
FIG. 2B provides image quantification of FIG. 2A showing Notch 1 expression in adipose tissue.
Figure 2C:
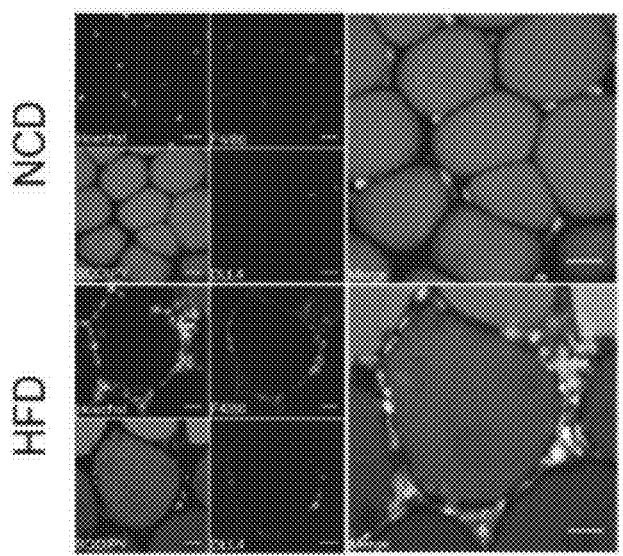
FIG. 2C presents confocal micrographs of DLL4 staining of whole mount epididymal fat (scale bar=20 μm).
Figure 2D:
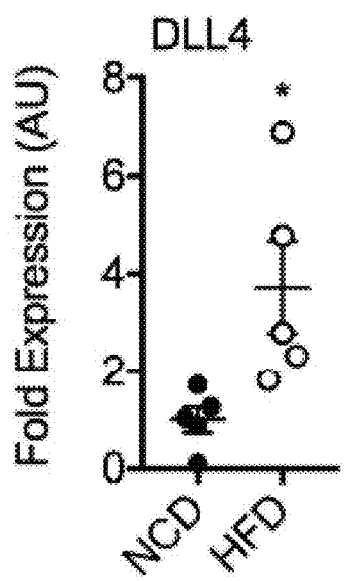
FIG. 2D provides image quantification of FIG. 2C showing DLL4 in adipose tissue. The values in FIG. 2B and FIG. 2D are shown as mean±SEM and are from a single experiment representative of 2 independent experiments with 5 mice per experimental group.
Figure 2E:
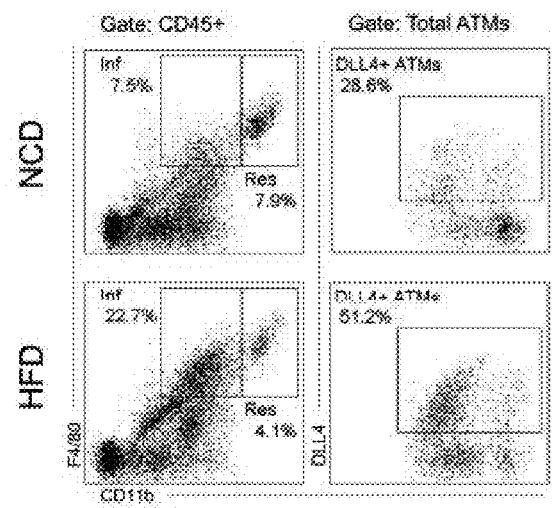
FIG. 2E presents flow cytometry dot plots of DLL4+ ATMs in epididymal fat. $CD11b^{int}$ are denoted as infiltrating ("Inf") and $CD11b^{hi}$ are denoted as resident ("Res").
Figure 2F:
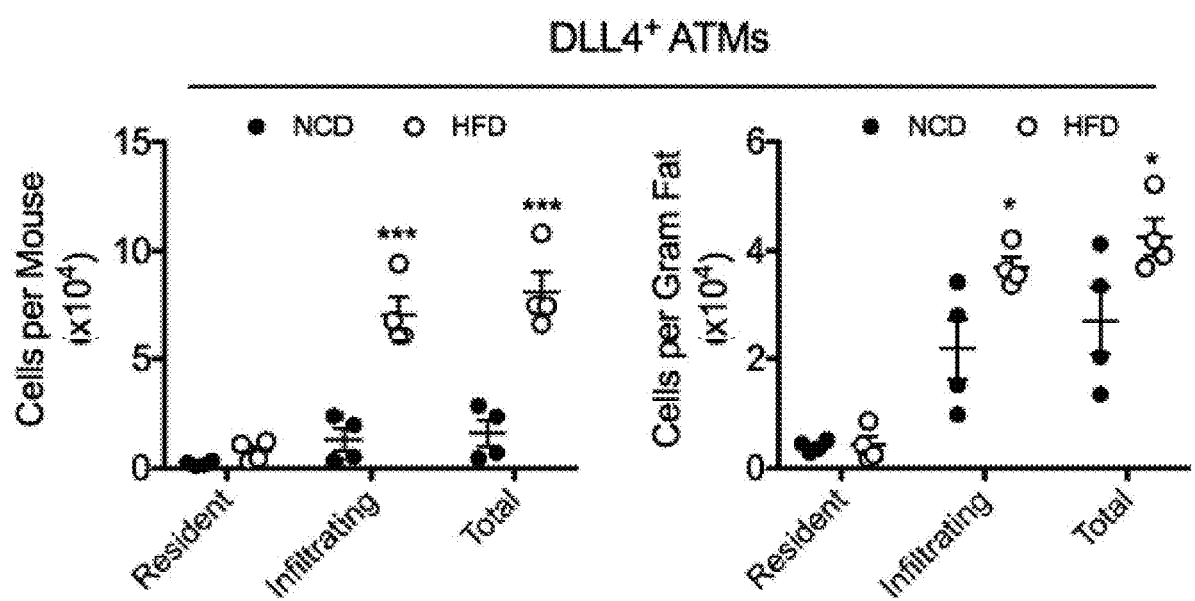
FIG. 2F presents the quantification of DLL4+ ATM cell counts represented per mouse and per gram fat. Values are presented as mean±SEM and are from a single experiment representative of 2 independent experiments with 4 biological replicates (pools of 1-6 mice) per experimental group. Statistical significance was determined by Student's t-test. $*p<0.05$, $p<0.01$, $*p<0.001$.

When potential target molecules for miR-30 were looked at, it was found through in silico analyses that miR-30 may target the 3'UTR of Dll4. Previous studies had confirmed miR-30-Dll4 targeting using luciferase reporter assay. Interestingly, DLL4 has been shown to be involved in Notch signaling. To that end, expression of Notch1 and the miR-30 target DLL4 in adipose tissue was evaluated. Notch1 and DLL4 were visualized in whole-mounted epididymal fat by confocal microscopy (FIG. 2A, FIG. 2C). Adipose tissue expression of DLL4 but not Notch1 was elevated in HFD-fed mice (FIG. 2B, FIG. 2D). Flow cytometry analysis of epididymal fat stromal vascular fractions (SVF) was then used to confirm that DLL4 expression was elevated on ATMs (CD45+/CD11b+/F4/80+/DLL4+) (FIG. 2D, FIG. 2F). Specifically, elevated DLL4 expression was most pronounced in the CD45+/CD11b$^{int}$/F4/80+ subset of infiltrating ATMs (FIG. 2F).

Figure 3A:
FIG. 3A schematically illustrates an in vitro experimental timeline during which differentiated bone marrow-derived microphages (BMDM) were incubated in conditioned medium from 3T3-L1 adipocytes (CM-3T3-L1A) prior to transfection with microRNA inhibitor locked nucleic acids (LNA) and subsequent culture. Cells and supernatants were harvested at 48 h.
Figure 3B:
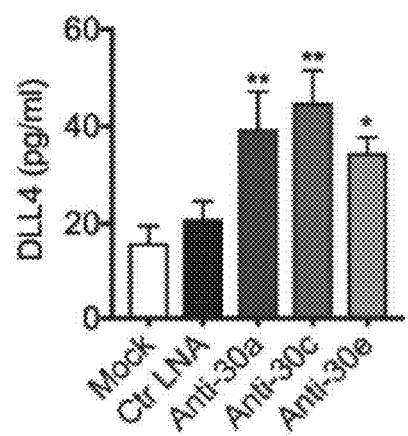
FIG. 3B presents the amounts of DLL4 detected in culture supernatants by ELISA during the in vitro experiments.
Figure 3C:
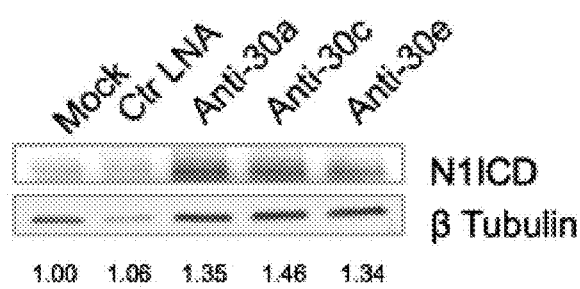
FIG. 3C presents Western blot results of cleaved/activated Notch1 (N1ICD) during the in vitro experiments. Fold induction relative to Mock is represented below each lane.
Figure 3D:
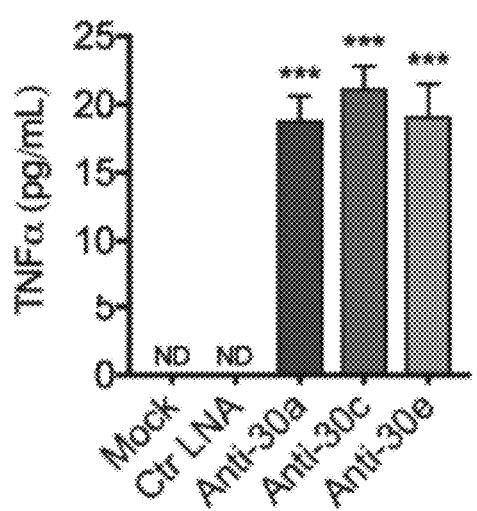
FIG. 3D presents the concentration of pro-inflammatory cytokine TNFα detected in culture supernatants by ELISA.
Figure 3E:
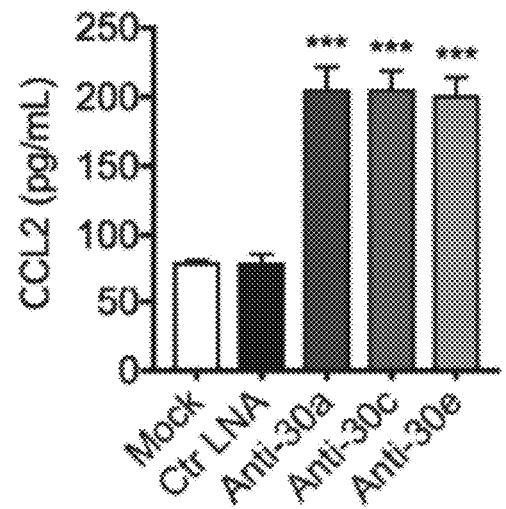
FIG. 3E presents the concentration of pro-inflammatory cytokine CCL2 detected in culture supernatants by ELISA. Data presented are mean±SEM of 3 independent experiments. Statistical significance was determined by one-way ANOVA with Bonferroni post hoc correction. $*p<0.05$, $p<0.01$, $*p<0.001$ vs. Mock.
Figure 3F:
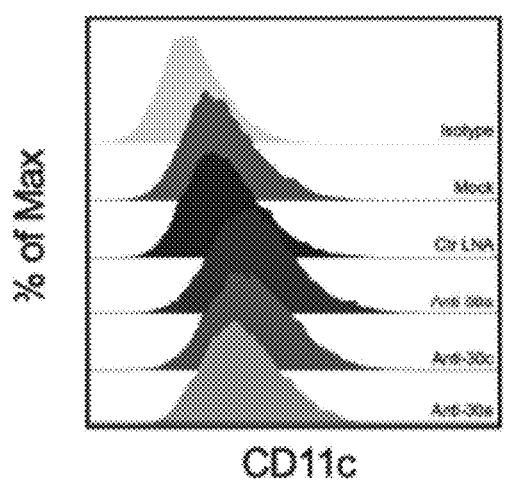
FIG. 3F presents flow cytometry histograms of CD11c expression in the transfected BMDM. For FIG. 3B-FIG. 3F, values are presented as mean±SEM and are from a single experiment representative of 2-3 independent experiments.
Figure 3G:
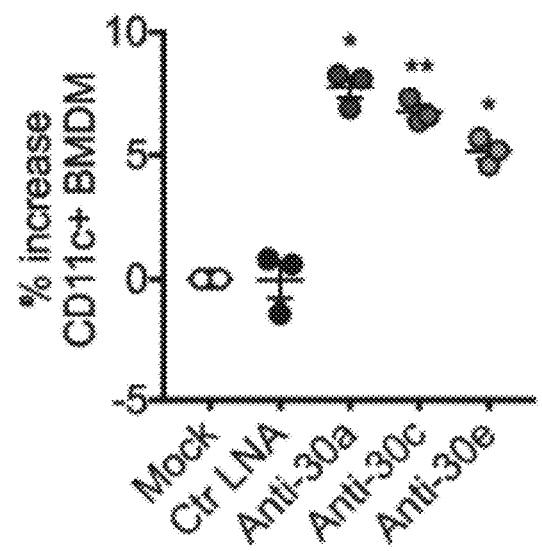
FIG. 3G presents the percentage increase in CD11c+ macrophages during the in vitro experiments.

To further demonstrate involvement of miR-30 in regulation of DLL4-mediated Notch signaling and pro-inflammatory response in macrophages, an in vitro assay was developed to mimic the downregulated miR-30 expression observed in vivo in obese ATMs. To that end, naïve bone marrow derived macrophages (BMDM) were cultured in conditioned medium from differentiated 3T3-L1 adipocytes (CM-3T3-L1A) to confer an ATM-like phenotype, and then transfected with miRNA inhibitor locked nucleic acids (LNA) which targeted miRs-30a-5p (Anti-30a), -30c-5p (Anti-30c), and -30e-5p (Anti-30e) (FIG. 3A). BMDM transfected with Anti-30a, Anti-30c, and Anti-30e LNAs had decreased expression of miRs-30a-5p, -30c-5p, and -30e-5p relative to Mock and control LNA (Ctr LNA)-transfected controls, although the inhibitors displayed some cross-reactivity. Anti-30a, Anti-30c, and Anti-30e transfection increased DLL4 and activated Notch1 intracellular domain (N1ICD) expression compared to Mock and Ctr LNA (FIG. 3B, FIG. 3C). Pro-inflammatory cytokines TNFα and CCL2 were also elevated in culture supernatants of inhibitor-transfected cells (FIG. 3D, FIG. 3E). Moreover, miR-30 inhibitors promoted increased surface expression of CD11c (FIG. 3F, FIG. 3G). Treatment of transfected cells with the Notch/γ-secretase inhibitor DAPT reduced induction of CD11c in miR-30 inhibitor-transfected cells. Specific blockade of DLL4 signaling using anti-DLL4 antibody also reduced induction of pro-inflammatory cytokines TNFα and CCL2 in miR-30 inhibitor-transfected cells. Conversely, lentiviral overexpression of miR-30a-5p in the RAW264.7 macrophage cell line reduced M1 polarization evidenced by decreased expression of CD11c and decreased TNFα and CCL2 production. Together these data demonstrated that miR-30 plays an anti-inflammatory role in macrophages by regulating DLL4-Notch1 signaling, M1 polarization and pro-inflammatory cytokine production in macrophages.

Figure 4A:
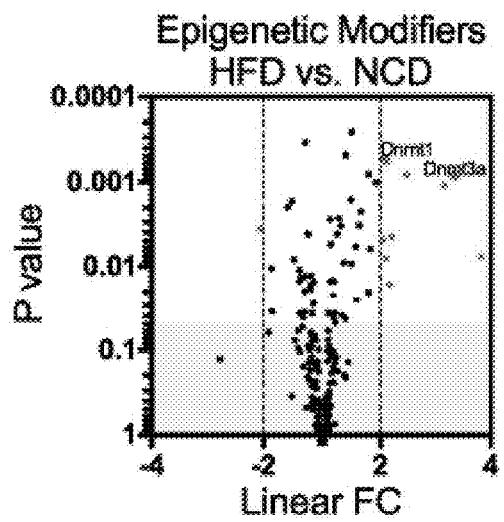
FIG. 4A presents a volcano plot displaying linear fold change of genes encoding epigenetic modification enzymes and factors. Fold change and p value observations were extracted from transcriptome microarrays.
Figure 4C:
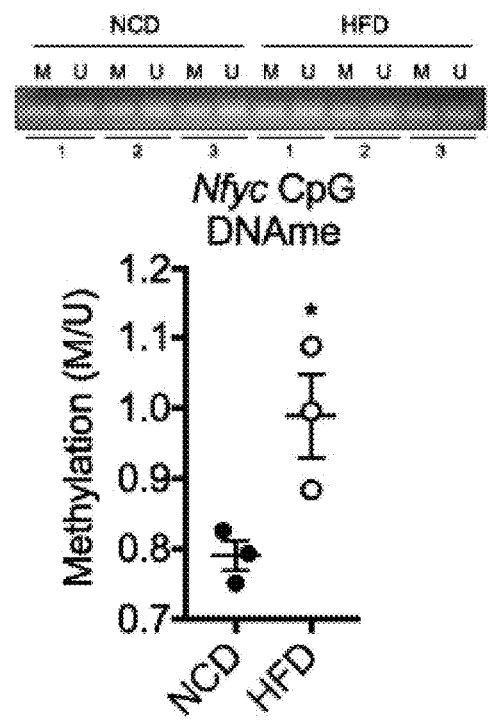
FIG. 4C presents the methylation-specific PCR quantification of DNA methylation (DNAme) in the Nfyc promoter CpG island. For FIG. 4A and FIG. 4C, values presented are representative of 3 independent experiments with 20 pooled NCD mice and 10 pooled HFD mice per experiment.
Figure 4B:
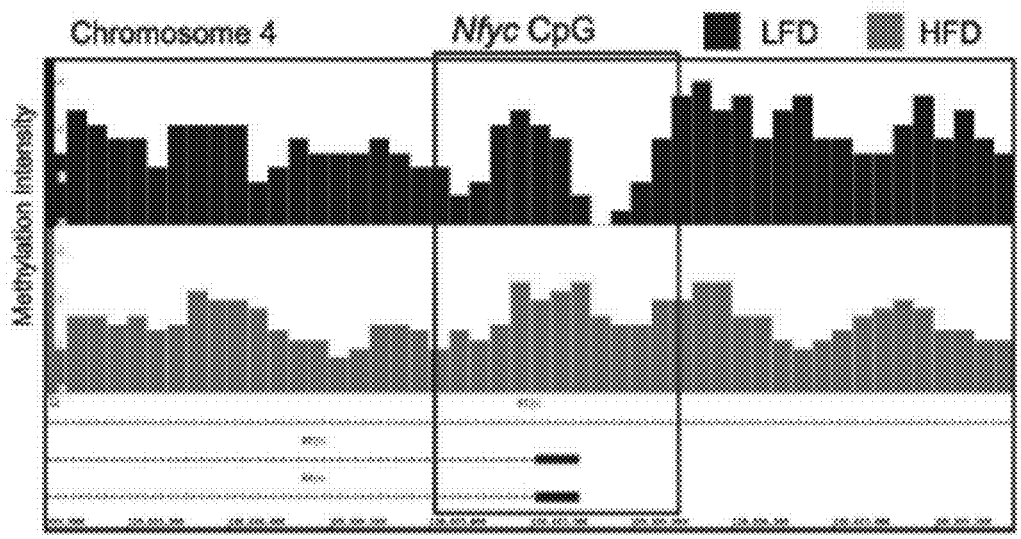
FIG. 4B presents IGB visualization of meDIP-seq peak intensity of DNA methylation in the Nfyc promoter CpG island. Data are representative of one experiment of 60 pooled LFD and 30 pooled HFD mice. Statistical differences were determined by using Student's t-test. $*p<0.05$, $p<0.01$, $*p<0.001$.

Epigenetic modifications can occur due to various environmental factors such as stress, aging, and diet. Because this study involved diet-induced obesity, epigenetic mechanisms that may control miR-30 expression in ATMs were investigated. Data from transcriptome microarrays enriched for epigenetic modification enzymes and factors revealed that gene expression of Dnmt1 and Dnmt3a were upregulated in ATMs of HFD vs. NCD-fed mice (FIG. 4A). Therefore, DNA methylation intensity of miR-30 gene regions was investigated. Mir30c-1 and mir30e are located within the same intron of the Nfyc gene, which contains a CpG island in its promoter region. Mir30a and mir30c-2 are intergenic miRNA genes that do not have any nearby CpG islands, therefore it was not possible to identify DNA methylation as a potential epigenetic mechanism regulating their expression. Methylated-DNA immunoprecipitation sequencing was performed (MeDIP-seq) to screen genome-wide DNA methylation in ATMs and DNA hypermethylation was found in the Nfyc-promoter CpG island in HFD- versus LFD-ATMs indicating expression of miRs-30c and -30e may be regulated by DNA methylation. This was validated in NCD- and HFD-ATMs by methylation-specific PCR (FIG. 4C). Together, these data indicated DNA methylation-dependent downregulation of miR-30 may promote pro-inflammatory polarization of adipose tissue macrophages during obesity.

While certain embodiments of the disclosed subject matter have been described using specific terms, such description is for illustrative purposes only, and it is to be understood that changes and variations may be made without departing from the spirit or scope of the subject matter.

What is claimed is:

1. A method for preferentially polarizing macrophages, the method comprising delivering a composition comprising a microRNA-30 or a polynucleotide encoding the microRNA-30 to adipose tissue macrophages, wherein the delivery leads to a decrease in M1 polarization of the adipose tissue macrophages.

2. The method of claim 1, wherein the microRNA-30 is a primary microRNA-30, a precursor microRNA-30, or a mature microRNA-30.

3. The method of claim 1, wherein the composition is a pharmaceutical preparation.

4. The method of claim 1, the microRNA-30 or the polynucleotide encoding the microRNA-30 being carried by a pharmaceutically acceptable carrier.

5. The method of claim 4, the pharmaceutically acceptable carrier comprising a virus, a liposome, a nanoparticle, a polymer, or any combination thereof.

6. The method of claim 1, wherein the microRNA-30 includes a microRNA-30a, a microRNA-30b, a microRNA-30c, a microRNA-30d, a microRNA-30e, or a combination thereof.

7. The method of claim 1, wherein the microRNA-30 includes a microRNA-30a, a microRNA-30b, a microRNA-30d, a microRNA-30e, or a combination thereof.

8. A method for decreasing expression of at least one of TNFα and CCL2 from a population of adipose tissue macrophages, the method comprising delivering a composition comprising a microRNA-30 or a polynucleotide encoding the microRNA-30 to the population of adipose tissue macrophages, wherein the delivery leads to a decrease in expression of at least one of the TNFα and the CCL2 from the population.

9. The method of claim 8, wherein the microRNA-30 is a primary microRNA-30, a precursor microRNA-30, or a mature microRNA-30.

10. The method of claim 8, wherein the composition is a pharmaceutical preparation.

11. The method of claim 8, wherein the microRNA-30 includes a microRNA-30a, a microRNA-30b, a microRNA-30c, a microRNA-30d, a microRNA-30e, or a combination thereof.

12. The method of claim 8, wherein the microRNA-30 includes a microRNA-30a, a microRNA-30b, a microRNA-30d, a microRNA-30e, or a combination thereof.

13. A method comprising delivering a composition comprising an anti-microRNA-30 or a polynucleotide encoding the anti-microRNA-30 to adipose tissue macrophages.

14. The method of claim 13, the anti-microRNA-30 comprising an anti-microRNA-30a, an anti-microRNA-30c, or an anti-micro-RNA-30e.

15. The method of claim 14, the anti-microRNA-30 comprising SEQ ID NO: 2, SEQ ID NO: 3, or SEQ ID NO:4.

16. The method of claim 13, wherein the delivery leads to elevation of expression of at least one of TNFα and CCL2.

17. The method of claim 13, wherein the delivery leads to an increase in M1 polarization of the adipose tissue macrophages.

18. The method of claim 13, wherein the composition is a pharmaceutical preparation.

19. The method of claim 13, wherein the anti-microRNA-30, includes an anti-microRNA-30a, an anti-microRNA-30b, an anti-microRNA-30d, an anti-microRNA-30e, or a combination thereof.

* * * * *

SEQUENCE LISTING

```
<160> NUMBER OF SEQ ID NOS: 8

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
taacacgtct atacgccca                                                  19

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ttccagtcga ggatgtttac                                                 20

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ctgagagtgt aggatgtt                                                   18

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 4
tccagtcaag gatgtttac                                                19

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ttcgttaatg ggagaaagtt c                                             21

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ctaccgccgc catattata                                                19

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7 tttttgtta atgggagaaa gttt                                           24

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
actctaccac caccatatta ta                                            22
```